US006121310A

United States Patent [19]

Ono et al.

[11] Patent Number: 6,121,310
[45] Date of Patent: Sep. 19, 2000

[54] AFLATOXIN CONTAMINATION INHIBITOR AND AFLATOXIN CONTAMINATION-INHIBITING METHOD

[75] Inventors: Makoto Ono, Kawasaki; Akinori Suzuki, Chigasaki; Akira Isogai; Shouhei Sakuda, both of Chiba, all of Japan

[73] Assignee: Morinaga Co. Ltd., Tokyo, Japan

[21] Appl. No.: 09/145,299

[22] Filed: Sep. 2, 1998

[30] Foreign Application Priority Data

Sep. 2, 1997 [JP] Japan .................................... 9-252720

[51] Int. Cl.[7] ........................... A01N 43/36; A61K 31/40

[52] U.S. Cl. ........................................... 514/422; 514/423

[58] Field of Search .............................................. 514/422

[56] References Cited

U.S. PATENT DOCUMENTS 5,773,263 6/1998 Ono et al. ............................... 435/118

FOREIGN PATENT DOCUMENTS

B45-17156 6/1970 Japan .

OTHER PUBLICATIONS

Fukunaga et al., Abstract to Nogyo Gijutsu Kenkyusho Hokoku, Byori Konchu No. 22, 1–94, 1968.
Kono et al., Abstract to J. Antibiot. (Tokyo), 21(7), 433–438, 1968.

*Tetrahedron Letters,* vol. 38, No. 2, 1997, Elsevier Science, Ltd., pp. 7399–7402, “Structure of Blasticidin A,” Shohei Sakuda, et al.

*The Journal of Antibiotics,* vol. 50, No. 2, Feb. 1997, Japan Antibiotics Research Association, pp. 111–118, “Aflastatin A, a Novel Inhibitor of Aflatoxin Production by Aflatoxigenic Fungi,” Makoto Ono et al.

*Journal of the American Chemical Society,* vol. 118, No. 33, 1996, pp. 7855–7856, “Aflastatin A, a Novel Inhibitor of Aflatoxin Production of *Aspergillus parasiticus,* from Streptomyces,” Shohei Sakuda, et al.

*Primary Examiner*—Dwayne C. Jones
*Attorney, Agent, or Firm*—Smith Gambrell & Russell, LLP

[57] ABSTRACT

An aflatoxin contamination inhibitor, which contains an actibiotic Blasticidin A of the following chemical formula (1) or its salt, (1)

and at least one selected from a solid carrier, a liquid carrier and an emulsion dispersant; and a method for inhibiting aflatoxin contamination by spraying a chemical containing from 10 to 5,000 ppm of the Blasticidin A or its salt on plants.

8 Claims, 4 Drawing Sheets

AFLATOXIN CONTAMINATION INHIBITOR AND AFLATOXIN CONTAMINATION-INHIBITING METHOD

BACKGROUND OF THE INVENTION (1) Field of the Invention

The present invention relates to an aflatoxin contamination inhibitor, which contains an antibiotic Blasticidin A or its salt as an active ingredient, and an aflatoxin contamination-inhibiting method using it.

(2) Background Information

Aflatoxin produced from some mildew belonging to Aspergillus sp. is known to have a potent carcinogenicity. Further, such aflatoxin producing-mildew have been known to infect agricultural commodities such as corn or peanuts and produce aflatoxin, resulting in contamination of these agricultural commodities.

As pharmaceuticals intended to prevent the aflatoxin contamination, dichlorovos and antibiotic Iturin A have heretofore been known. These pharmaceuticals are used to prevent aflatoxin contamination by controlling the propagation of aflatoxigenic fungi.

SUMMARY OF THE INVENTION

However, the pharmaceuticals which control the propagation of aflatoxigenic fungi, have a problem that once drug-resistant strains emerge, such pharmaceuticals are no longer capable of inhibiting the pervasion thereof, and accordingly these drugs have not been practiced until now.

It is an object of the present invention to provide an aflatoxin contamination inhibitor or a aflatoxin contamination-inhibiting method using it, by which aflatoxin contamination can effectively be prevented.

In Japanese Patent Application No. 8-73258 (corresponding to U.S. Pat. No. 5,773,263), the present inventors have conducted research on antibiotics which inhibit the biosynthesis of this compound by aflatoxigenic fungi in order to prevent aflatoxin contamination. The purpose is to minimize the possibility of emergence and pervasion of drug-resistant strains from the aflatoxigenic fungi, by inhibiting only the biosynthesis of aflatoxin without inhibiting the growth of the aflatoxigenic fungi. Namely, such a purpose is based on the following theory. The production of aflatoxin by the aflatoxigenic fungi is not indispensable biochemical demand for the growth of said strains. Accordingly, it is expected that, by the use of pharmaceuticals which inhibit only biosynthesis of aflatoxin, selection of the resistant strains by the pharmaceuticals themselves does not occur, and the pervasion of the resistant strains can be inhibited.

As a result of the above researches, the present inventors have succeeded in isolating a novel antibiotic, Aflastatin A having an activity of inhibiting the production of aflatoxin, from the culture medium of some strains which belong to Streptomyces sp. MRI 142, FERM BP-5841 collected from a soil sample in Zushi-shi, Kanagawa prefecture, Japan.

However, it has been found from the researches made afterwards that Aflastatin A is similar in the physical and chemical properties to Blasticidin A which has been known, but the chemical structure of which has not been known.

With respect to Blasticidin A, for example, Japanese Patent Publication No. 45-17156 discloses that Blasticidin A has an antimicrobial activity against e.g. various bacteria and phytopathogenic fungi, but does not disclose whether or not Blasticidin A shows effects for inhibiting the production of aflatoxin.

Accordingly, the present inventors have analyzed the chemical structure of Blasticidin A, and conducted tests for inhibiting the production of aflatoxin by using Blasticidin, and as a result, they have found that Blasticidin A is a compound having a different chemical structure from that of Aflastatin A and showing an inhibitory action of the production of aflatoxin at the same level as Aflastatin A. The present invention has been accomplished based on the discovery.

Namely, an object of the present invention is to provide an aflatoxin contamination inhibitor, which contains an antibiotic Blasticidin A of the following chemical formula (1), or its salt, as an active ingredient, and an aflatoxin contamination-inhibiting method using it.

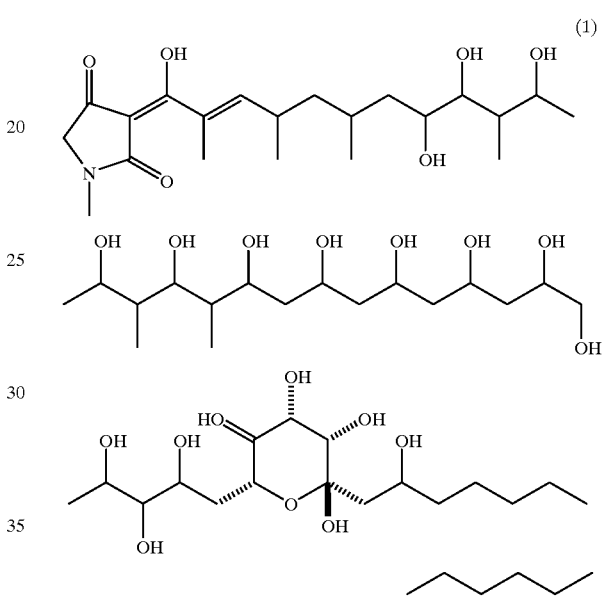

The antibiotic Blasticidin A or its salt of the present invention, intensely inhibits the production of aflatoxin by the aflatoxigenic fungi such as *Aspergillus parasiticus* and exhibits excellent effects for inhibiting aflatoxin contamination by the aflatoxigenic fungi, as indicated in the examples as shown below.

Further, Blasticidin A is produced from the strains for the production thereof with a productivity of as high as from 15 to 18 times the productivity of Aflastatin A, and is advantageous from the viewpoint of production costs.

DETAILED DESCRIPTION OF THE INVENTION

Figure 1:
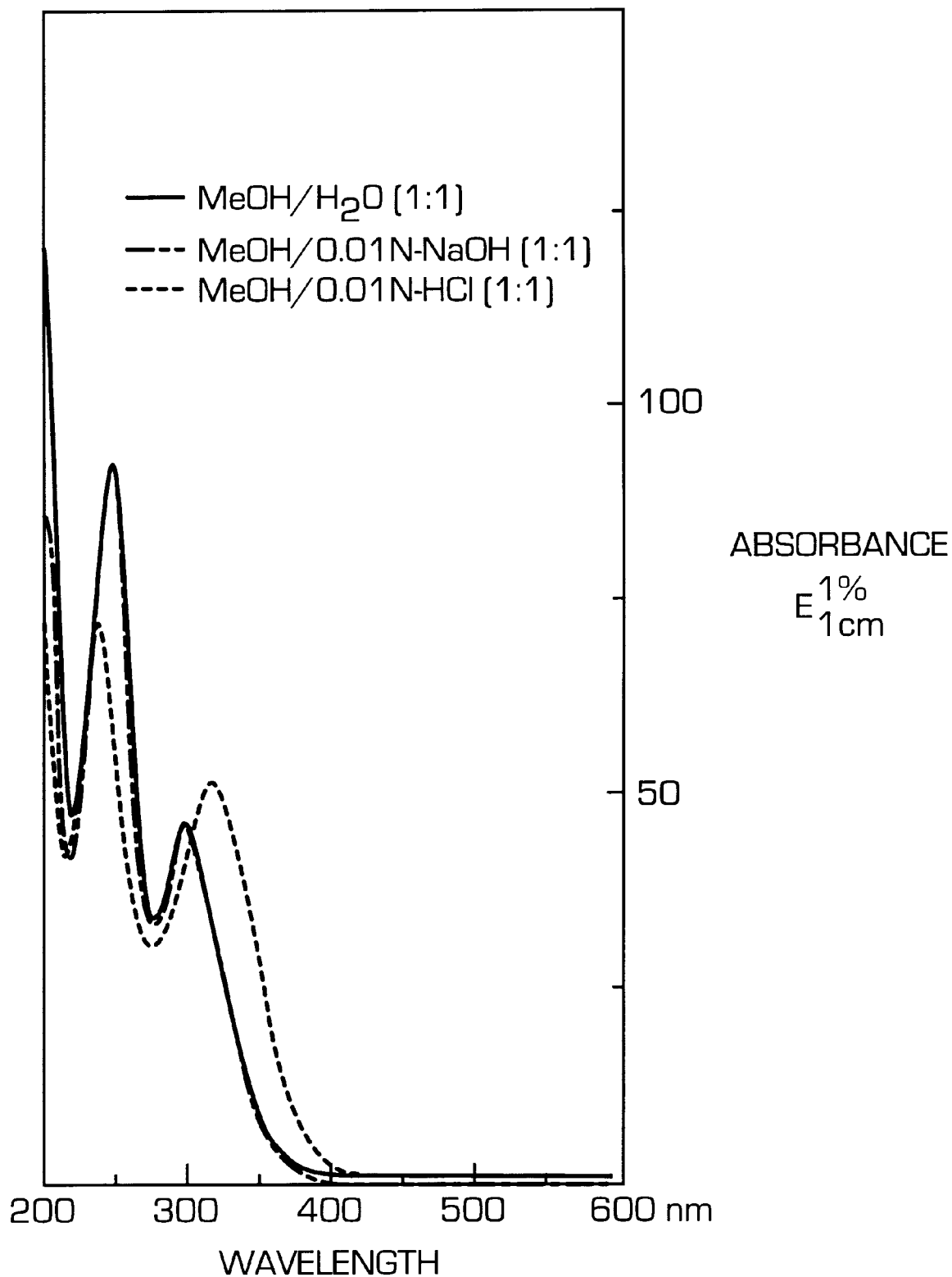
FIG. 1 is a graph showing an ultraviolet absorption spectrum of a diethylamine salt of the antibiotic Blasticidin A of the present invention.

Physico-chemical properties and biological properties of the Blasticidin A as an active ingredient of the aflatoxin contamination inhibitor of the present invention, are as follows:

a) Appearance: white powder
b) Molecular formula: $C_{58}H_{107}O_{23}N$
c) Specific rotation
$[\alpha]^{22}_{D=+}10.8°$ (C=1.0, DMSO)
d) Molecular weight: 1257
FAB-MASS m/z 1208.7153 (M+Na)+
e) Major UV spectrometry
UV spectra of Blasticidin A in the form of a diethylamine salt are shown in FIG. 1.

Figure 2:
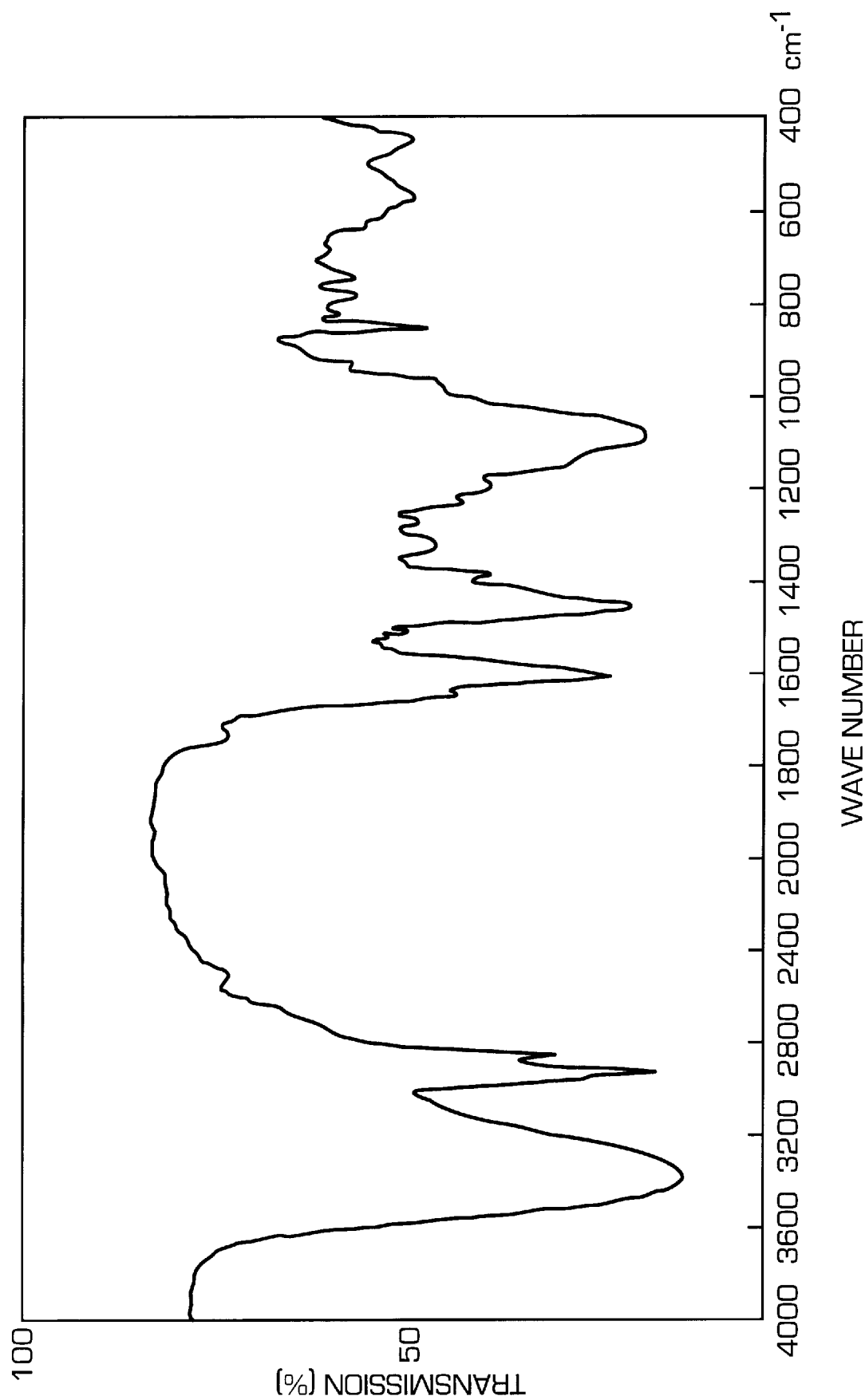
FIG. 2 is a graph showing an infrared absorption spectrum of a diethylamine salt of the antibiotic Blasticidin A.
Figure 3:
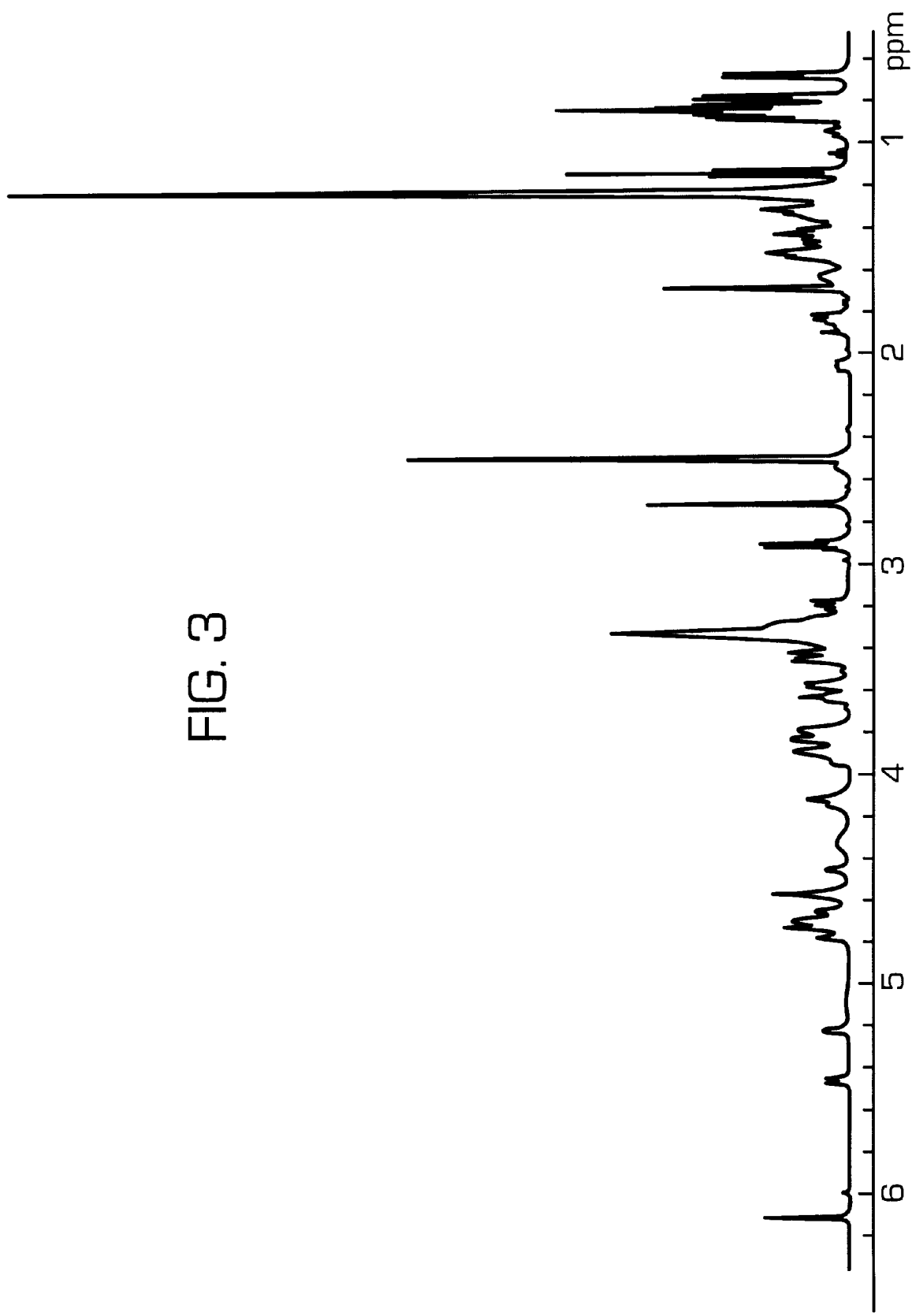
FIG. 3 is a graph showing $^1$H-NMR spectrum of the antibiotic Blasticidin A.
Figure 4:
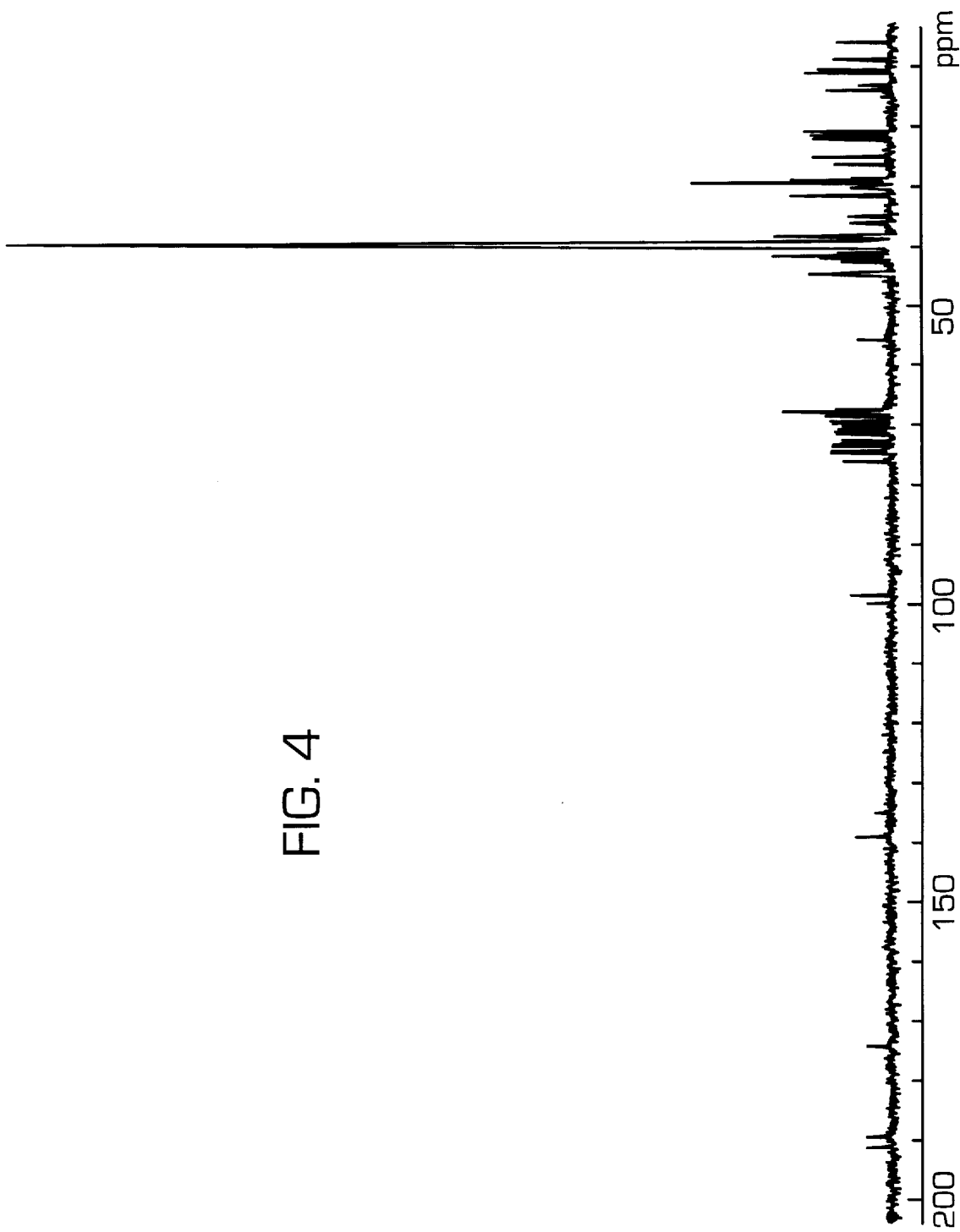
FIG. 4 is a graph showing $^{13}$C-NMR spectrum of the antibiotic Blasticidin A.

| | |
|---|---|
| λmax (MeOH/H$_2$O, 1:1) | nm(E$^{1\%}_{1\,cm}$); 299(49), 247(89) |
| (MeOH/0.01N—NaOH, 1:1) | nm(E$^{1\%}_{1\,cm}$); 299(49), 247(88) |
| (MeOH/0.01N—HCl, 1:1) | nm(E$^{1\%}_{1\,cm}$); 314(58), 237(63) | f) Major IR spectrometry
IR spectra of Blasticidin A in the form of a diethylamine salt on a potassium bromide wafer are shown in FIG. 2.

g) NMR spectra
$^1$H-NMR spectrum of the Blasticidin A in the form of a diethylamine salt in DMSO-d$_6$ at 500 MHz are shown in FIG. 3.
$^{13}$C-NMR spectrum of the Blasticidin A in the form of a diethylamine salt in DMSO-d$_6$ at 125.65 MHz are shown in FIG. 4.

h) Solubility
Soluble in DMSO (dimethyl sulfoxide); slightly soluble in methanol, aqueous ethanol, aqueous butanol and glycerol; hardly soluble in water and other organic solvents i) Color reaction
Positive to ferric chloride reaction
Negative to ninhydrin reaction The antibiotic Blasticidin A is prepared by, for example, culturing Blasticidin A-producing strains which belong to Streptomyces sp, and isolating Blasticidin A from the cultured medium.

As the Blasticidin A-producing strains, *Streptomyces griseochromogenes* IFO 13413 may, for example, be mentioned. The above fungi are available from the Institute for Fermentation, Osaka (17-85, Juso-honmachi 2-chome, Yodogawa-ku, Osaka-shi, Japan). Further, Blasticidin A may be produced in accordance with, for example, the methods as described in Japanese Patent Publication No. 45-17156.

Namely, Blasticidin A is produced by propagating Blasticidin A-producing strains in a nutrient medium containing anabolic carbon sources and nitrogen sources under aerobic condition by, for example, shake culture or liquid culture.

Preferred carbon sources for the nutrient medium are glucose, starch, sucrose and glycerol. Further, preferred nitrogen sources are yeast extract, peptone, gluten powder, cotton seed powder, soy bean powder, corn steep liquor, dried yeast and wheat malt; ammonium salts such as ammonium nitrate, ammonium sulfate and ammonium phosphate; and inorganic and organic nitrogen compounds such as urea and amino acid. It is preferred to use the carbon sources and nitrogen sources in combination. However, there is no necessity to use the ones of high purity, and the ones of low purity may be used so long as they contain a small amount of growth factors and a substantial amount of inorganic nutrients.

Further, as the case requires, an inorganic salt such as sodium carbonate, calcium carbonate, sodium phosphate, potassium phosphate, sodium chloride, potassium chloride, sodium iodide, potassium iodide, magnesium salts, copper salts, cobalt salts, zinc salts or iron salts, may be added to the medium.

Further, particularly when the medium markedly foams, an antifoaming agent such as liquid paraffin, fatty oil, vegetable oil, mineral oil or silicone, may be added.

When Blasticidin A is produced in a large scale, it is preferred to use a submerged culture, as in the methods preferred for the mass production of other bioactive substances. Further, when produced in a small scale, it is preferred to conduct shake culture in a flask, a bottle or the like, or surface culture.

Further, when the culture is carried out in a large size tank, it is preferred to use propagation type Blasticidin A-producing strains for the inoculation to the production tank in order to avoid the delay in growth in the Blasticidin A-producing process. Accordingly, it is preferred to inoculate spores or mycelia of Blasticidin A-producing strains to a medium of a relatively small amount, and culture the inoculated medium, thereby producing a seed culture of the Blasticidin A producing-strains, and then to transfer the produced seed culture to a large size tank. The medium used for the production of the propagation type inoculation material may be substantially the same as or different from the medium used for the production of the Blasticidin A.

As for the stirring and aeration of a culture mixture, various methods may be employed. For example, a method wherein a propeller or a similar mechanical stirring device is used, a method wherein a fermentation tank is rotated or shaken, or a method wherein sterile air is blown to the medium, may preferably be used.

Fermentation is preferably carried out at a temperature of from 20 to 37° C., more preferably from 25 to 37° C., for from 50 to 200 hours. It is preferred to determine the temperature and period of time from these ranges depending upon the various conditions and size for the fermentation.

After completion of the fermentation, Blasticidin A is recovered from the culture medium, and, as the case requires, purified it. However, the method is not particularly limited. For example, a method wherein solvent extraction is carried out by using one or more solvents, and the extract is relatively concentrated by evaporation, distillation or the like, and then the concentrate is purified by precipitation, recrystallization, chromatography or the like, may be employed. When the solvent extraction is carried out, for example, an organic solvent such as methanol, dimethylsulfoxide, butanol, ethyl acetate or acetone, may preferably be used.

In the production method of the present invention, particularly, when calcium carbonate is added to a nutrient medium for production, since Blasticidin A is found mainly in the cultured mycelia, it is preferred to collect the mycelia by filtration or centrifugal separation of the culture medium, and then extract the Blasticidin A from the strains by solvent extraction.

In the present invention, as the method for producing the salt of Blasticidin A, various methods may be employed. For example, the following methods may be employed. Namely, first the Blasticidin A as obtained above is contacted with or dissolved in a solution of a compound or an element which exhibits basicity in usual solvents, for example, organic ones such as dimethylamine, diethylamine or ammonia, or inorganic ones such as sodium, calcium or magnesium. Then, the reaction product is purified by a usual method, for example, recrystallization, precipitation or chromatography, to obtain a salt of the Blasticidin A.

When the antibiotic Blasticidin A and its salt is used as a control agent for the purpose of inhibiting aflatoxin contamination, it can be formulated into the desired formulation such as granules, dusting powder, emulsion, wettable powder, tablets, lubricant, spraying agent or fuming agent for use, by using a suitable solid carrier, liquid carrier, emulsifier or the like, as usual agricultural formulations known in the technical field. Among the carriers, as the solid carrier, clay, kaolin, bentonite, acid clay, diatomaceous earth, calcium carbonate, nitrocellulose, starch, carboxymethylcellulose and the like are preferably used. As the liquid carrier, water, methanol, ethanol, ethylene glycol, glycerol, dimethyl sulfoxide and the like are preferably used.

Further, during the formulation, as the case requires, generally used adjuvants, for example, sulfates of higher alcohols, polyoxyethylenealkyl allyl ether, alkylally polyethylene glycol ester, alkylallyl sorbitan monolaurate, alkylally sulfonate, quaternary ammonium salt, polyalkylene oxide, and deoxycholic acid salt and its ester, may be incorporated.

When the aflatoxin contamination inhibitor of the present invention is used, the proportion of the antibiotic Blasticidin A or its salt is controlled taking into consideration the types of the infection bacteria or pathogenic bacteria and extent of propagation thereof. However, in general, it is preferred to control the concentration to the level of from 10 to 5,000 ppm, preferably from 50 to 500 ppm for use.

The present invention will be described in further detail with reference to examples. However, it should be mentioned that the present invention is not limited to these. In the examples, "%" in medium represents weight/volume % unless otherwise specified.

EXAMPLE 1

Production of Blasticidin A 125 ml of a liquid seed medium containing 3% of sucrose, 1.5% of soy bean meal, 0.08% of $K_2HPO_4$, 0.02% of $MgSO_4.7H_2O$ and 0.4% of $CaCO_3$, was adjusted to pH 7.20, and then poured into each of 500 ml-Erlenmeyer flasks, followed by sterilization at 121° C. for 15 minutes.

Then, on the sterilized medium, one platinum loop of *Spreptomyces griseochromogenes* IFO 13413 strain on a matured slant culture was inoculated. The flask was shaken by a rotary shaker at 27° C. for 42 hours with a 5 cm throw at 160 rpm.

Separately, 4 liters of a liquid production medium material 1 (hereinafter referred to as medium material 1) containing 1.875% of soy bean meal, 0.1% of $K_2HPO_4$, 0.025% of $MgSO_4.7H_2O$ and 0.5% of $CaCO_3$, was adjusted to pH 7.20, and then poured into a 10 liters-jar fermentor, followed by sterilization at 121°C. for 20 minutes. Further, 1 liter of a liquid production medium material 2 (hereinafter referred to as medium material 2) was sterilized at 121° C. for 20 minutes separately from the medium material 1.

The sterilized medium materials 1 and 2 were cooled to not more than 60° C., and then the whole amount of the medium material 2 was added under sterilized conditions into a 10 liter-jar fermentor having the medium material 1 placed.

Then, 250 ml of the above liquid seed medium was inoculated on 5 liters of the above liquid production medium, followed by cultivation at 27° C. for 144 hours with the supply of air at a rate of 5 liters/min. with stirring of 400 rpm. During the cultivation, an anti-foaming agent "Ainol" (tradename, manufactured by Aible K.K.) was automatically dropwise added by an automatic anti-foaming agent dropping device.

4.3 liters of the resulting culture broth was filtered by a filter paper "Toyo Roshi No. 2"(manufactured by Toyo Roshi K.K.), and the mycelial cake on the filter paper was collected by washing with 1 liter of distilled water. Then, the obtained mycelial cake was dipped in 1.2 liters of methanol and stirred at 65° C. for 1 hour for solvent extraction, followed by filtration by a glass filter to separate the extract from the mycelial cake. Then, the mycelial cake was recovered and subjected to extraction operation further two times with methanol under the same conditions as above.

The whole amount of the resulting extracts (3.3 liters) were concentrated at 60° C. under reduced pressure to obtain 118 g of a brown tar-like substance. The tar-like substance was dissolved in 600 ml butanol saturated with water and washed twice with 300 ml of 0.5 w/v% sodium bicarbonate with a separatory funnel, followed by washing with 300 ml of distilled water to recover a butanol layer (an upper layer). Then, the recovered butanol layer was concentrated at 60° C. under reduced pressure to obtain 113 g of a brown oily substance.

To the oily substance, 400 ml of a mixed liquid of chloroform-methanol (3:1) was poured to obtain a precipitate. This precipitate was left to stand in the dark at room temperature overnight for maturity of the precipitate, and then subjected to filtration by a glass filter. 300 ml of tetrahydrofuran was poured on the glass filter for washing and recovering the precipitated substance on the filter. Then, the recovered insolubles were dried in air in the dark to obtain 9830 mg of purified Blasticidin A.

21 mg of the resulting Blasticidin A was dissolved in 30 ml of a mixed solution of a 0.5 v/v % diethylamine aqueous solution and methanol (4:6), and filtrated by a filter "Milex FG" (tradename, manufactured by Nihon Millipore Ltd.). Then, 2 ml thereof was subjected to high performance liquid chromatography using a reverse phase column "CAPCELL PACK 18 AG120"(tradename, manufactured by Shiseido K.K.) with 15 mm in diameter and 250 mm in length. Elution was carried out at room temperature with a mixed solution of a 0.5 v/v % diethylamine aqueous solution and methanol (37:63) at a flow rate of 5.0 ml/min., whereupon a single peak of Blasticidin A was observed at around 5 minutes. The operation of recovering the single peak was repeated 15 times, and the recovered fractions were concentrated under reduced pressure, followed by lyophilization to obtain 14 mg of a diethylamine salt of Blasticidin A.

In the above operation, since the solubility of the Blasticidin A in the developing solvent was limitative, it was impossible to treat the whole amount of 9830 mg of the purified Blasticidin A obtained from 4.3 liters of the culture, with the high performance liquid chromatography. Theoretically, however, by the repetition of the above operation, about 6881 mg of a diethylamine salt of Blasticidin A is to be obtained from 9830 mg of purified Blasticidin A, namely, 4.3 liters of the culture. This is at least 15 times the productivity of Aflastatin A as the prior invention. Namely, as disclosed in Japanese Patent Application No. 8-73258, Aflastatin A shows the productivity of only about 450 mg per 4.3 liters under the substantially same conditions.

EXAMPLE 2

Aflatoxin Production Inhibitory Activity of Blasticidin A

Spores of *Aspergillus parasiticus* NRRL 2999 strains as aflatoxigenic fungi, which were cultured on a slant medium of potato dextrose agar (manufactured by Nihon Suisan K.K.) at 27° C. for 21 days, were scraped off and suspended in an aqueous solution of a 0.01% surfactant "Tween 80" (tradename, manufactured by ICI Co.) which was sterilized at 121° C. for 15 minutes to prepare a spore suspension.

5.0 mg of the Blasticidin A obtained in Example 1 was dissolved in 10 ml of dimethyl sulfoxide for dilution, and then filtrated by a sterilized filter "Dimex" (tradename, manufactured by Nihon Millipore Ltd.), followed by sterilization to prepare a test solution.

10 μl of the test solution was sterilized at 121°C. for 15 minutes, added to 10 ml of potato dextrose agar medium (manufactured by Nihon Suisan K.K.) maintained at 60° C., stirred and then poured into a sterilized Petri dish having an internal diameter of 9 cm, to prepare dilution series plates of agar medium of the test solution. At this time, the final concentration of the Blasticidin A was 0.5 μg/ml, 0.125 μg/ml or 0.031 μg/ml. As a control, 10 μl of dimethyl sulfoxide was added to 10 ml of potato dextrose agar medium in the same manner as the above. As described above, three pieces of each of test plates and control plates having respective concentrations were prepared.

On one point at the center of each plate, 10 μl of the spores suspension obtained above was inoculated. The number of the inoculated strains was $2.5 \times 10^4$ per plate. These plates were incubated at 27° C. for 7 days. At the 7th day, the growth conditions of the aflatoxigenic fungi were observed by measuring the diameter of colonies. Then, the whole amount of the agar medium including the strains were scraped off the Petri dishes for the measurement test of aflatoxin content.

Quantitative determination of the aflatoxin was carried out in accordance with the method described in J. Assoc. Off. Anal. Chem., 68, 458–461 (1985). Namely, to the samples scraped off the Petri dishes, 80 ml of chloroform was added and vigorously stirred by a Waring blender for extraction of aflatoxin, and then filtrated by a filter paper "Toyo Roshi No. 5A" (tradename, Toyo Roshi K.K.) for recovery of the extract, followed by addition of anhydrous sodium sulfate for dehydration. 20 ml of this extract was collected by using a pipette, and subjected to a florisil column "SEP-PAK FLORISIL CARTRIDGES" (tradename, Nihon Millipore Ltd.,). Then, the column was washed with 30 ml of a mixed solution of chloroform and methanol (9:1), and eluted with 50 ml of a mixed solution of acetone and water (99:1) to recover the aflatoxin. Then, the elute of the mixed solution of acetone and water (99:1) was dried to dryness under reduced pressure to prepare a test sample for high performance liquid chromatography. The above operations were carried out under a fluorescent lamp which generates no ultraviolet rays, and brown glass appliances were used.

Then, the above test sample was dissolved in 5 ml of a mixed solution of tetrahydrofuran, water and acetic acid, and 25 μl thereof was subjected to a column for high performance liquid chromatography "COSMOSIL 5-Phenyl" (tradename, Nakarai Tesk Co.) of 4.6 mm in diameter and 150 mm in length, followed by high performance liquid chromatography wherein elution was carried out at a flow rate of 0.8 ml/min. by using a mixed solution of tetrahydrofuran and water (20:80). Quantitative determination of aflatoxin was carried out by comparing the area of isolated peak of 365 nm ultraviolet absorption with that of a standard product.

Aflatoxin production inhibitory activities of the Blasticidin A are indicated in Table 1. In Table 1, the colony diameter and the aflatoxin concentration were represented by the average of triplicated experiments±standard deviation. Further, the aflatoxin concentration was calculated as the total of four homologues of aflatoxin, B1, G1, B2 and G2 (hereinafter the same applies).

TABLE 1

| Blasticidin A (μg/ml) | Colony diameter (cm) | Concentration of aflatoxin (total of B1, G1, B2 and G2 μg/ml) |
|---|---|---|
| Control (0) | 8.1 ± 0.1 | 13.75 ± 0.81 |
| 0.031 | 7.9 ± 0.2 | 7.24 ± 1.88 |
| 0.125 | 7.1 ± 0.5 | 1.11 ± 0.70 |
| 0.500 | 4.0 ± 0.3 | Not detected |

From the results given in Table 1, by the addition of Blasticidin A or the increase of the concentration of Blasticidin A, the production of aflatoxin can be remarkably reduced. The aflatoxin production-inhibitory effect indicated in Table 1 is substantially the same as the aflatoxin production-inhibitory effect by Aflastatin A in Japanese Patent Application No. 8-73258 proposed by the present inventors.

As described above, the aflatoxin contamination inhibitor of the present invention, contains an antibiotic Blasticidin A or its salt, as an active ingredient. The Blasticidin A and its salt have aflatoxin contamination-inhibitory effect at substantially the same level as the Aflastatin A disclosed in Japanese Patent Application No. 8-73258, as evident from the above examples. Further, Blasticidin A can be produced with an extremely high productivity compared to Aflastatin A, and is therefore advantageous from the viewpoint of production cost.

What is claimed is:

1. A method for inhibiting aflatoxin contamination, comprising:
   contacting plants or plant products with a composition comprising 10 to 5,000 ppm of Blasticidin A, or anactive salt thereof.

2. The method according to claim 1, wherein the composition comprises 50 to 500 ppm of Blasticidin A, or an active salt thereof.

3. The method according to claim 1, wherein the plants or plant products are crops or other agricultural products subject to aflatoxin contamination.

4. A method of inhibiting aflatoxin contamination of plants and plant products, comprising:
   contacting the plants and plant products with an amount of Blasticidin A, or an active salt thereof, effective to inhibit production of aflatoxin in aflatoxigenic organisms.

5. The method according to claim 4, wherein the amount of Blasticidin A or active salt thereof does not affect the growth of the aflatoxigenic organisms.

6. The method according to claim 4, wherein the amount of Blasticidin A, or active salt thereof, does not select for aflatoxigenic organisms resistant to the effects of the method.

7. The method according to claim 4, wherein the plants and plant products are crops or other agricultural commodities.

8. A method for inhibiting aflatoxin production in aflatoxigenic organisms, comprising:
   contacting the aflatoxigenic organisms with an amount of Blasticidin A, or an active salt thereof, sufficient to inhibit production of aflatoxin, without inhibiting the growth of the aflatoxigenic organisms.

* * * * *